United States Patent [19]

Omatsu et al.

[11] Patent Number: 4,713,488

[45] Date of Patent: Dec. 15, 1987

[54] METHOD FOR PRODUCING CYCLOALKYL AMINOPHENOL DERIVATIVES

[75] Inventors: Masayuki Omatsu; Naoki Yonese, both of Nishinomiya; Mitsuru Kondo, Hyogo, all of Japan

[73] Assignee: Kanzaki Paper Manufacturing Co., Ltd., Tokyo, Japan

[21] Appl. No.: 786,546

[22] Filed: Oct. 11, 1985

[30] Foreign Application Priority Data

Oct. 23, 1984 [JP] Japan ................................ 59-223587

[51] Int. Cl.$^4$ .............................................. C07C 85/08
[52] U.S. Cl. ...................................... 564/397; 564/398
[58] Field of Search ................................ 564/397, 398

[56] References Cited

U.S. PATENT DOCUMENTS 3,209,030 9/1965 Bicek .................................... 564/398
3,541,153 11/1970 Sandridge ........................... 564/398

FOREIGN PATENT DOCUMENTS 552102 1/1958 Canada ................................ 564/398
1468362 3/1977 United Kingdom ............... 564/398

OTHER PUBLICATIONS

Sidgwick, N. V., *The Organic Chemistry of Nitrogen*, 3rd Ed., Oxford, 1966, pp. 155–156.

*Primary Examiner*—Charles F. Warren
*Assistant Examiner*—John A. Sopp
*Attorney, Agent, or Firm*—Wenderoth, Lind & Ponack

[57] ABSTRACT

Cycloalkyl aminophenol derivatives are produced by reacting o-, m- or p-aminophenol with a cycloalkanone having 5 to 12 carbon atoms in the presence of a reducing agent and preferably with the addition of an acid.

4 Claims, No Drawings

METHOD FOR PRODUCING CYCLOALKYL AMINOPHENOL DERIVATIVES

FIELD OF THE INVENTION

This invention relates to an improved method for producing cycloalkyl aminophenol derivatives. More particularly it relates to an improved method for producing cycloalkyl aminophenol derivatives with a high yield in a simple manner.

DESCRIPTION OF THE PRIOR ART

Cycloalkyl aminophenol derivatives are known as intermediates for the preparation of dyes for use in pressure-sensitive record materials or heat-sensitive record materials.

For the production of such cycloalkyl aminophenol derivatives, there have been various proposals as hereunder mentioned:

(i) a method in which one mole of resorcinol or hydroquinone is heat-reacted with one or two moles of cycloalkylamine in or without the presence of anhydrous magnesium chloride or anhydrous magnesium chloride or anhydrous zinc chloride, (ii) a method in which cycloalkylamine, aminophenol hydrochloride or cycloalkylamine hydrochloride, and aminophenol are subjected to heat-reaction in or without the presence of anhydrous zinc chloride, and (iii) a method in which aminophenol is heat-reacted with a cycloalkylating agent such as p-toluene sulfonic acid-cycloalkyl or -halogenated cycloalkyl in the presence of a base.

However, in addition to the fact that the yield of such cycloalkyl aminophenol derivatives under any of said known methods is low, namely from 40 to 60%, there is also the problem that elevated temperature of nearly 200° C. is required for the heat-reaction in both the known methods (i) and (ii), and in the known method (iii) p-toluenesulfonic acid etc. will be by-produced in large amount.

Further, these known methods are accompanied with another problem that a costly cycloalkylamine or cycloalkylating agent is required to be used when cycloalkyl aminophenol derivatives other than cyclohexylaminophenol are to be produced, whereby the product unavoidably becomes costly.

SUMMARY OF THE INVENTION

The present inventors have conducted extensive studies in order to solve the problems in the aforementioned known methods and in order to develop an improved method by which a cycloalkyl aminophenol derivative may be produced with a remarkable yield in a simple manner. As a result, it has been found that when an aminophenol derivative is reacted with a cycloalkanone in the presence of a reducing agent, the objective cycloalkyl aminophenol derivative can be effectively produced with highly improved yield. On the basis of this finding, this invention has been completed.

It is therefore an object of this invention to provide an improvement in the known methods for the production of cycloalkyl aminophenol derivatives.

A further object of this invention is to provide an improved method by which cycloalkyl aminophenol derivatives can be effectively produced with highly improved yield.

DETAILED DESCRIPTION OF THE INVENTION

The cycloalkyl aminophenol derivatives provided according to this invention are compounds of the general formula:

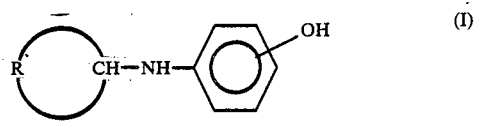

wherein R is a saturated hydrocarbon radical having 4 to 11 carbon atoms.

Examples of the compounds represented by the general formula (I) are, for example, N-cyclohexyl-m-aminophenol, N-(3-methylcyclohexyl)-m-aminophenol, N-(4-methylcyclohexyl)-m-aminophenol, N-cyclopentyl-m-aminophenol, N-(4-t-butylcyclohexyl)-m-aminophenol, N-(2,3-dimethylcyclohexyl)-m-aminophenol, N-(2-i-propyl-5-methylcyclohexyl)-m-aminophenol, N-(3,5,5-trimethylcyclohexyl)-m-aminophenol, N-cycloheptyl-m-aminophenol, N-cyclododecyl-m-aminophenol, N-(2-methylcyclohexyl)-m-aminophenol, etc.

These compounds are known and they are also known as being useful intermediates particularly for the production of dyes for use in pressure-sensitive record materials or heat-sensitive record materials.

The method of producing these cycloalkyl aminophenol derivatives according to this invention may be represented by the following reaction scheme:

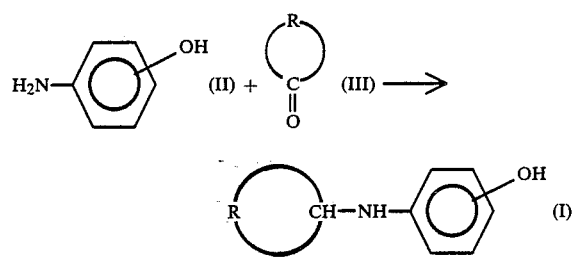

wherein R is a saturated hydrocarbon radical having 4 to 11 carbon atoms.

The aminophenol derivatives of the general formula (II) are known, and they are o-aminophenol, m-aminophenol and p-aminophenol.

The cycloalkanone derivatives of the general formula (III) are also known, and they are, for example, cyclopentanone, 2-cyclopentylcyclopentanone, cyclohexanone, 2-methylcyclohexanone, 3-methylcyclohexanone, 4-methylcyclohexanone, 4-t-butylcyclohexanone, 2-n-hexylcyclohexanone, 2,5-dimethylcyclohexanone, 3,4-dimethylcyclohexanone, 3,5-dimethylcyclohexanone, 3,3,5-trimethylcyclohexanone, 3,5,5-trimethylcyclohexanone, menthone, 3,3,5,5-tetramethylcyclohexanone, cycloheptanone, cyclooctanone, cyclododecanone, camphor, santenone, etc.

Among these cycloalkanones or their derivatives, cyclopentanone is the most preferred, for the reasons that it is highly soluble in water, and is economic since not only water but also an aqueous solution containing less than 20%/vol. of alcohol, which does not invite any problem of environmental pollution, can be effectively used as the reaction solvent when it is used as a reactant.

The reaction of an aminophenol derivative of the general formula (II) with a cycloalkanone derivative of the general formula (III) to produce a cycloalkyl aminophenol derivative of the general formula (I) in this invention is carried out in the presence of a reducing agent at a temperature of from 5° C. to 150° C., preferably from 5° C. to 50° C., under either atomospheric pressure or elevated pressure.

When the reaction is carried out under elevated pressure, it is preferred to be less than 10 kg/cm$^2$.

In order to sufficiently achieve the foregoing objects of this invention, the cycloalkanone derivative for the reaction with the aminophenol derivative is preferably used in an amount of 0.9 to 2.0, more preferably 1.0 to 1.5 molar ratio, versus one mole of the aminophenol derivative, and the two compounds and the reducing agent are dispersed or dissolved in a reaction solvent followed by the reaction at a temperature in the above range while stirring the mixture.

The addition of the cycloalkanone to the mixture is preferred to be carried out either by intermittently adding a partial amount over several times or by drop-wise supplying it so that the amount is always maintained at a predetermined amount in the reaction mixture during the reaction operation.

The above reaction can be carried out in the presence of an acid in the reaction mixture, to increase the yield of the product further while effectively preventing the generation of undesirable by-products.

Usable as the acid are, for example, an inorganic acid such as a mineral acid e.g. hydrochloric acid, sulfuric acid or phosphoric acid, or an organic acid such as an alkanoic acid containing 1 to 5 carbon atoms e.g. acetic acid or formic acid.

Such acid is usually added to the mixture to be reacted which is composed of an aminophenol derivative of the general formula (II), a cycloalkanone of the general formula (III), a reducing agent and a reaction solvent.

The kind of the acid to be used and its amount to be employed are determined appropriately in accordance with the reducing agent and the reaction solvent to be used.

The isolation of the objective cycloalkyl aminophenol derivative generated in the reaction mixture can be practiced by any known manner such as distillation, crystallization or extraction.

Usable as the reducing agent are reducing agents which generate so-called nascent hydrogen such as a mixture of a metal such as zinc, iron or tin with an acid such as hydrochloric acid, sulfuric acid or acetic acid, a mixture of a metal such as zinc or iron with an alkali substance such as sodium hydroxide or potassium hydroxide, and a mixture of a metal such as sodium, lithium, aluminium, magnesium or zinc with an alcohol such as methanol, ethanol or propanol, or water; lower metallic compounds such as stannous chloride, ferrous sulfate, ferrous hydroxide or titanium trichloride; oxygen acceptable non-metallic compounds such as sodium polysulfide, sodium sulfite, sodium bisulfite, sodium thiosulfate or hydrosulfite; alcoholates such as sodium methylate, sodium ethylate, aluminium ethylate or aluminium isopropylate; metallic hydrogen compounds such as sodium borohydride or lithium aluminium hydride; or a combination of a catalytic hydrogenation agent and hydrogen which is used in the known catalytic reduction reaction.

Among these reducing agents, the combination of a catalytic hydrogenation agent and hydrogen is the most desirable from the viewpoint that it not only can be easily handled in the process operation but also brings about a higher yield of the product.

Usable as the catalytic hydrogenation agent to be used together with hydrogen are nickel catalyst such as Raney nickel, reduced nickel, a carrier supported nickel catalyst such as nickel supported on diatomaceous earth, alumina, silica, silica gel or terra abla, and a modified catalyst in which the nickel of the carrier supported nickel catalyst is modified with sulfur or a sulfur-containing compound; iron catalysts such as Raney iron or reduced iron; cobalt catalyst such as Raney cobalt, reduced cobalt or cobalt-carrier catalyst; copper catalyst such as Raney copper, reduced copper or copper-carrier catalyst; palladium catalyst such as palladium black, palladium oxide, colloidal palladium, palladium . carbon, palladium . barium sulfate or palladium . barium carbonate; platinum catalyst such as platinum black, colloidal platinum, spongy platinum, platinum oxide, platinum sulfide, platinum-carrier catalyst such as platinum . carbon; rhodium catalyst such as colloidal rhodium, rhodium . carbon and rhodium oxide; ruthenium catalyst; rhenium catalyst such as rhenium heptoxide or rhenium . carbon; copper chromate catalyst; molybdenum oxide catalyst; vanadium oxide catalyst; tungsten oxide catalyst; molybdenum sulfide catalyst or tungsten sulfide catalyst.

Among these catalytic hydrogenation agents, palladium . agents are especially preferred and among those, palladium . carbon is the most preferred.

However, in the practice of this invention, any of said reducing agents can be optionally used.

In the case when the foregoing reducing agents other than the combination of a catalytic hydrogenation agent and hydrogen are used, a member or a mixture of two or more members selected from these reducing agents may be employed. The amount to be applied is determined with due regard to the kind of the reducing agent to be employed. However it is preferred to use an excess over the stoichiometric amount.

In the case when the aforesaid combination of a catalytic hydrogenation agent and hydrogen is used, said catalytic hydrogenation agent is used usually at a ratio of from 0.0005 to 0.6 gram-atom, and preferably at a ratio of from 0.001 to 0.3 gram-atom, based on the metallic atom of the catalytic hydrogenation agent versus one mole of the aminophenol derivative to be used. And as for the acid, its amount to be used is usually 0.8 to 1.2 more preferably 0.9 to 1.1 equivalents versus one equivalent of the aminophenol derivative to the mixture.

In that case, the yield of the objective cycloalkyl aminophenol is remarkably raised and the generation of by-products is remarkably prevented.

However, in the case where the amount of the acid is below 0.8 equivalent versus one equivalent of the aminophenol derivative, the generation of by-products increases, and where the amount of the acid exceeds 1.2 equivalents versus one equivalent of the aminophenol derivative the progress of the reaction becomes slower.

Usable as the reaction solvent in this invention are, for example, water, ether such as ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, triethylene glycol dimethyl ether, triethylene glycol diethyl ether, tetrahydrofuran, dioxane, diethyl ether, dipropyl ether or diphenyl ether, ester such as ethyl acetate, propyl acetate, ethylene glycol diacetate, diethylene glycol diacetate or triethylene glycol diacetate, alcohol such as methanol, ethanol, isopropanol, ethylene glycol, diethylene glycol, triethylene glycol or propylene glycol, aromatic hydrocarbon such as benzene, toluene, xylene or cumene, carboxylic acid such as acetic acid or propionic acid.

In this invention, these reaction solvents can be used either alone or in combination.

The amount of such reaction solvent to be used is usually from 0.5 to 20 parts by weight, and preferably from 1.0 to 8 parts by weight, based on the amount of the aminophenol derivative to be used.

PREFERRED EMBODIMENTS OF THE INVENTION

The advantages of this invention are now described in more detail by reference to the following Examples, which are provided here for illustrative purposes only, and are not intended to limit the scope of this invention.

Unless otherwise indicated, parts and % signify parts by weight and % by weight respectively.

EXAMPLE 1

Production of N-cyclopentyl-m-aminophenol 21.8 g (0.2 mol) of m-aminophenol and 25.2 g (0.3mol) of cyclopentanone were dissolved in a mixture composed of 20 cc of distilled water and 10 cc of concentrated hydrochloric acid. The resultant solution was cooled to 20° C., and 40 g of zinc powder was added. Then after 40 cc of concentrated hydrochloric acid was added, it was reacted at 20° C. for 60 minutes while being stirred. Successively 10 cc of concentrated hydrochloric acid was added and the reaction was continued for 30 minutes. After the reaction was completed, the reaction mixture was neutralized with aqueous solution of sodium hydroxide followed by extraction with toluene. The extract was distilled to separate toluene and the residue was purified by reduced pressure distillation to afford 18.1 g of a pale-yellowish viscous fluid product having a boiling point of 127° C. to 130° C./1 mmHg with the yield of 51%, which was identified to be N-cyclopentyl-m-aminophenol by I.R. and N.M.R. spectroscopy.

EXAMPLE 2

Production of N-cyclopentyl-m-aminophenol 21.8 g (0.2 mol) of m-aminophenol was dissolved in a mixture composed of 200 cc of distilled water and 10 cc of concentrated hydrochloric acid, and the resultant solution was cooled to 20° C. After 40 g of zinc powder was added thereto, a one-fourth quantity of 25.2 g of cyclopentanone as well as a one-fourth quantity of 50 cc of concentrated hydrochloric acid were added to the mixture intermittently every 20 minutes in four times while the mixture was being stirred, then the reaction mixture was held at 20° C. for 30 minutes while being stirred. Successive procedures were practiced in the same way as Example 1 to afford 29.4 g of a pale-yellowish viscous fluid product having a boiling point of 127° C. to 130° C./1 mmHg with the yield of 83%, which was identified to be N-cyclopentyl-m-aminophenol by I.R. and N.M.R. spectroscopy.

EXAMPLE 3

Production of N-cyclododecyl-m-aminophenol 21.8 g (0.2 mol) of m-aminophenol and 43.8 g (0.24 mol) of cyclododecanone were dissolved in 80 cc of acetic acid followed by the addition of 40 g of zinc powder, and the resultant mixture was refluxed for 3 hours. After the reaction was completed, the reaction mixture was neutralized with aqueous solution of sodium hydroxide and extracted with toluene. The extract was distilled to separate toluene therefrom, then the residue was subjected to recrystallization from methanol to afford 22.8 g of a colorless crystalline product having a melting point of 133° C. to 135° C. with the yield of 43%, which was identified to be N-cyclododecyl-m-aminophenol by I.R. and N.M.R. spectroscopy.

EXAMPLE 4

Production of N-cyclopentyl-m-aminophenol 21.8 g (0.2 mol) of m-aminophenol was dissolved in a mixture composed of 100 cc of methanol and 20 cc (0.23 mol) of concentrated hydrochloric acid, and the resultant solution was cooled to 10° C. After 3 g of palladium carbon (palladium content: 5%) was added thereto, a one-fifth quantity of 18.5 g (0.22 mol) of cyclopentanone was added intermittently every 20 minutes in five times while blowing hydrogen gas into the mixture and while the mixture was being stirred. After the addition of cyclopentanone was completed, the reaction was continued at 10° C. for an additional one hour while the reaction mixture was being stirred. After the reaction was completed, the reaction mixture was filtered to remove the catalyst therefrom, then the filtrate was neutralized and distilled to separate methanol.

The residue was dissolved in toluene, washed with distilled water and refluxed to separate toluene. The resultant liquid was subjected to reduced pressure distillation to afford 33.0 g of a pale-yellowish viscous fluid product having a boiling point of 127° C. to 130° C./1 mmHg with the yield of 93%, which was identified to be N-cyclopentyl-m-aminophenol by I.R. and N.M.R. spectroscopy.

EXAMPLE 5 TO 11

The procedures of Example 4 were repeated except that the cycloalkanones as shown in the following Table were used, and the yields of the corresponding cycloalkyl aminophenol derivatives are illustrated with their boiling points in the following Table.

TABLE

| | Cycloalkanone | Cycloalkyl aminophenol derivative | boiling point (°C.) | yield (%) |
|---|---|---|---|---|
| Example 5 | cyclohexanone | N—cyclohexyl-m-aminophenol | 155~158/3 mmHg | 92 |
| Example 6 | 3-methylcyclohexanone | N—3-methylcyclohexyl-m-aminophenol | 155~160/2 mmHg | 90 |
| Example 7 | 4-t-butylcyclohexanone | N—4-t-butylcyclohexyl-m-aminophenol | 180~184/3 mmHg | 88 |
| Example 8 | 2,3-dimethylcyclohexanone | N—2,3-dimethylcyclohexyl-m-aminophenol | 160~161/1 mmHg | 80 |
| Example 9 | 2-i-propyl-5-methyl-cyclohexanone (menthone) | N—2-i-propyl-5-methylcyclohexyl-m-aminophenol | 147~148/1 mmHg | 72 |
| Example 10 | 3,5,5-trimethyl-cyclohexanone | N—3,5,5-trimethylcyclohexyl-m-aminophenol | 156~158/1 mmHg | 89 |

| | Cycloalkanone | Cycloalkyl aminophenol derivative | boiling point (°C.) | yield (%) |
|---|---|---|---|---|
| Example 11 | cycloheptanone | N—cycloheptyl-m-aminophenol | 136~139/1 mmHg | 91 |

EXAMPLE 12

Production of N-(4-methylcyclohexyl)-m-aminophenol 21.8 g (0.2 mol) of m-aminophenol and 24.7 g (0.22 mol) of 4-methylcyclohexanone were dissolved in 100 ml of acetic acid, and the resultant solution was cooled to 10° C.

After 0.3 g of platinum oxide was added thereto, the mixture was reacted for two hours while blowing hydrogen gas thereinto. After the reaction was completed, the reaction mixture was filtered to remove the catalyst, then the filtrate was distilled to separate acetic acid. The residue was subjected to recrystallization from toluene to afford 27.9 g of colorless crystalline product having a melting point of 122° C. to 123° C. with the yield of 68%, which was identified to be N-(4-methyl-cyclohexyl)-m-aminophenol by I.R. and N.M.R. spectroscopy.

EXAMPLE 13

Production of N-cyclopentyl-m-aminophenol 21.8 g (0.2 mol) of m-aminophenol was dissolved in a mixture composed of 100 cc of distilled water and 20 cc (0.23 mol) of concentrated hydrochloric acid, and the resultant solution was cooled to 10° C.

After 3 g of palladium carbon (palladium content: 5%) was added thereto, a one-fifth quantity of 18.5 g (0.22 mol) of cyclopentanone was added intermittently every 20 minutes in five times while blowing hydrogen gas thereinto and while the mixture was being stirred. After the addition of cyclopentanone was completed, the reaction was continued at 10° C. for an additional one hour while the reaction mixture was being stirred. After the reaction was completed, the reaction mixture was filtered to remove the catalyst, then the filtrate was neutralized, followed by extraction with toluene. The extract was distilled to separate toluene and the residue was purified by reduced pressure distillation to afford 31.9 g of pale-yellowish viscous fluid product having a boiling point of 127° C. to 130° C./1 mmHg with the yield of 89.9%, which was identified to be N-cyclopentyl-m-aminophenol by I.R. and N.M.R. spectroscopy.

EXAMPLE 14

Production of N-cyclopentyl-m-aminophenol 21.8 g (0.2 mol) of m-aminophenol and 18.5 g (0.22 mol) of cyclopentanone were dissolved in a mixture composed of 18 cc (0.2 mol) of concentrated hydrochloric acid, 62 cc of distilled water and 10 cc of ethanol. The resultant mixture was charged into an autoclave, 4 g of palladium carbon (palladium content: 10%) was then added thereto, and the resultant mixture in the autoclave was cooled to 15° C. The autoclave was sealed, evacuated, purged with nitrogen and then replaced and pressurized with hydrogen gas to 5 kg/cm². The temperature of the contents of the autoclave was held at 15° C. to 20° C. for 7 hours while the contents were being stirred.

After the reaction was completed, the autoclave was vented, opened and the contents withdrawn and filtered to remove the catalyst. The resultant filtrate was neutralized and then extracted with toluene.

The extract was distilled to separate toluene therefrom, and the residue was subjected to reduced pressure distillation to afford 31.4 g of pale-yellowish viscous fluid product having a boiling point of 127° C. to 130° C./1 mmHg with the yield of 88.6%, which was identified to be N-cyclopentyl-m-aminophenol by I.R. and N.M.R. spectroscopy.

EXAMPLE 15

Production of N-cyclopentyl-m-aminophenol

The procedures of Example 14 were repeated except that the mixture composed of 18 cc of concentrated hydrochloric acid, 62 cc of distilled water and 10 cc of ethanol in Example 14 was replaced by a mixture composed of 10 cc (0.1 mol) of concentrated sulfuric acid and 80 cc of distilled water.

As a result, there was afforded 29.9 g of pale-yellowish viscous fluid product having a boiling point of 127° C. to 130° C./1 mmHg with the yield of 84.3%, which was identified to be N-cyclopentyl-m-aminophenol by I.R. and N.M.R. spectroscopy.

EXAMPLE 16

Production of N-cyclopentyl-m-aminophenol 21.8 g (0.2 mol) of m-aminophenol was dissolved in a mixture composed of 18 cc (0.2 mol) of concentrated hydrochloric acid, 62 cc of distilled water and 10 cc of ethanol. The resultant solution was charged into an autoclave, 4 g of palladium . carbon (palladium content: 10%) was then added thereto, and the mixture in the autoclave was cooled to 15° C. The autoclave was sealed, evacuated, purged with nitrogen and then replaced and pressurized with hydrogen gas to 5 kg/cm².

As the temperature of the contents of the autoclave was being maintained at 15° C. to 20° C. while the contents were being stirred, 18.5 g (0.22 mol) of cyclopentanone was continuously poured thereinto for 1.5 hours by plunger pump, then the reaction was continued at 15° C. to 20° C. for 3 hours while the contents were being stirred. After the reaction was completed, the autoclave was vented, opened and the contents withdrawn and filtered to remove the catalyst. The resultant filtrate was neutralized and then extracted with toluene. The extract was distilled to separate toluene therefrom, and the residue was subjected to reduced pressure distillation to obtain 33.6 g of pale-yellowish viscous fluid product having a boiling point of 127° C. to 130° C./1 mmHg with the yield of 94.8%, which was identified to be N-cyclopentyl-m-aminophenol by I.R. and N.M.R. spectroscopy.

We claim:

1. A method for producing a cycloalkyl aminophenol of the formula:

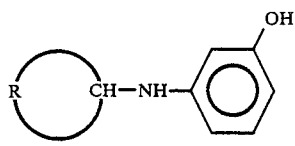

wherein R is a saturated hydrocarbon radical having 4 to 11 carbon atoms, which comprises reacting an aminophenol of the formula:

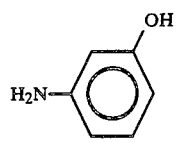

with a cycloalkanone of the formula:

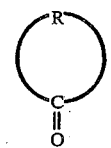

wherein R is as defined above, in the presence of a combination of a catalytic hydrogenation agent and hydrogen as a reducing agent, and an acid selected from the group consisting of mineral acids and alkanoic acids of 1 to 5 carbon atoms in an amount of 0.8 to 1.2 equivalents versus one equivalent of the aminophenol, at a temperature of from 5° C. to 50° C. and under a pressure of from atmospheric pressure to elevated pressure of less than 10 kg/cm$_2$.

2. A method according to claim 1 wherein the cycloalkanone is cyclopentanone.

3. A method according to claim 2 wherein the reaction is carried out in the presence of a reaction medium of water or aqueous solution containing less than 20%/vol of alcohol.

4. A method according to claim 1 wherein the reaction is carried out by intermittent or drop-wise addition of the cycloalkanone to the reaction system.

* * * * *